US00PP36644P2

(12) United States Plant Patent
Bédard

(10) Patent No.: US PP36,644 P2
(45) Date of Patent: May 6, 2025

(54) HYBRID TEA ROSE PLANT NAMED 'WEKamyldroder'

(50) Latin Name: *Rosa hybrida*
Varietal Denomination: WEKamyldroder

(71) Applicant: Early Morning LLC, Lawrenceburg, IN (US)

(72) Inventor: Christian Bédard, Rancho Cucamonga, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 18/947,826

(22) Filed: Nov. 14, 2024

(51) Int. Cl.
*A01H 5/02* (2018.01)
*A01H 6/74* (2018.01)

(52) U.S. Cl.
USPC ..... Plt./140

(58) Field of Classification Search
USPC ..... Plt./101, 130, 139, 140
See application file for complete search history.

(56) References Cited

U.S. PATENT DOCUMENTS

| | | | |
|---|---|---|---|
| PP8,494 | P | 12/1993 | Tracy |
| PP9,389 | P | 12/1995 | Winchel |
| PP22,469 | P2 | 1/2012 | Carruth |
| PP22,571 | P2 | 3/2012 | Carruth |
| PP23,324 | P2 | 1/2013 | Bedard |
| PP23,692 | P3 | 7/2013 | Bedard |
| PP29,273 | P2 | 5/2018 | Fryer |

OTHER PUBLICATIONS

Weeks Roses: In Love Again, Wholesale Rose Catalog, Weeks Roses, 2025. Retrieved from the Internet: <URL:http://www.weeksroses.com/downloads/Catalogs_Digital/_WR25_Catalog_Digital.pdf>, 76 pages.

*Primary Examiner* — Susan McCormick Ewoldt
(74) *Attorney, Agent, or Firm* — McKee, Voorhees & Sease, PLC

(57) ABSTRACT

A new variety of Hybrid Tea rose suitable for garden decoration, having flowers of medium red coloration.

1 Drawing Sheet

Classification: The present disclosure relates to a new *Rosa hybrida* plant.

Variety denomination: The new plant has the varietal denomination 'WEKamyldroder'.

BACKGROUND OF THE INVENTION

This invention relates to a new and distinct variety of Hybrid Tea Rose. It has as its seed parent the variety known as 'FRYrapture' (U.S. Plant Pat. No. 29,273) and as its pollen parent the variety known as 'WEKcharlie' (U.S. Plant Pat. No. 22,571).

SUMMARY OF THE INVENTION

Among the features which distinguish the new variety from other presently available and commercial rose cultivars known to the applicant are the following combinations of characteristics: its elegant flowers of medium red coloration, its abundant blooms, its excellent color stability throughout the life of the flower and its very glossy foliage. The plant has an upright slightly spreading growing habit, suitable for outdoor garden decoration.

Asexual reproduction of the new variety by budding as performed in Kern County, California, shows that the foregoing and other distinguishing characteristics come true to form and are established and transmitted through succeeding asexual propagations. 'WEKamyldroder' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'FRYrapture' by the following combination of characteristics: whereas 'WEKamyldroder' bears flowers of medium red coloration, 'FRYrapture' bears flowers of dark even pink coloration. The new variety has an upright slightly spreading medium height to somewhat tall growing habit (about 107 to about 163 cm. in height and about 102 to about 127 cm. spread at the widest point), whereas the seed parent has a bushy upright significantly taller (about 190 to about 240 cm. in height) and significantly wider (about 150 to about 180 cm. spread at the widest point) growing habit.

The new variety may be distinguished from its pollen parent, 'WEKcharlie' by the following combination of characteristics: whereas 'WEKamyldroder' bears very double flowers (about 24 to 58 petals), 'WEKcharlie' bears double flowers with significantly lesser petalage (about 20 to 26 petals). The new variety has an upright slightly spreading medium height to somewhat tall growing habit (about 107 to about 163 cm. in height and about 102 to about 127 cm. spread at the widest point), whereas the pollen parent has a moderately upright compact and rounded significantly shorter (about 85 to about 100 cm. in height) and significantly narrower (about 60 to about 70 cm. spread at the widest point) growing habit.

COMPARISON WITH THE CLOSEST COMMERCIALLY AVAILABLE CULTIVAR

The new variety may be distinguished from its closest commercially available cultivar, 'ADHarman' (not patented) by the following combination of characteristics: whereas 'WEKamyldroder' bears very double flowers (about 24 to 58 petals) with a moderate fruity fragrance, 'ADHarman' bears double flowers with a strong fruity rose fragrance and with lesser petalage (about 24 to 34 petals). The new variety has an upright slightly spreading medium height to somewhat tall growing habit (about 107 to about 163 cm. in height), whereas the closest commercially available cultivar has a bushy compact upright significantly shorter (about 80 to about 100 cm. in height) growing habit.

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, California in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, California in the month of November. Phenotypic expression may vary with environmental, cultural and climatic conditions, as well as differences in conditions of light and soil.

Flower

The new variety usually bears its flowers singly. Flowers are borne on strong somewhat short to moderately long stems (about 18 to about 80 cm.). Outdoors, the plant blooms abundantly and nearly continuously during the growing season. The flowers have a moderate fruity fragrance.

Bud

The peduncle is about 1.9 to about 8.2 cm. in length, of average to somewhat heavy caliper (about 0.3 to about 0.5 cm. in diameter), and usually erect. It is mostly smooth, with few stipitate glands, and few hairs. Peduncle color is between 146C and 148B often heavily suffused, especially on the side exposed to the sun, with between 187B and 187A.

Before the calyx breaks, the bud is about 1.2 to about 2.0 cm. in diameter at the widest point, about 1.6 to about 2.4 cm. in length, and somewhat pointed to moderately ovoid in shape. The surface of the bud bears between 15 to 22 foliaceous appendages with few stipitate glands and some hairs, usually with stout moderately cut foliaceous parts extending beyond the tip of the bud about ½ or more of its length. Bud color is between 137C and 147C sometimes lightly suffused, especially on the side exposed to the sun, with between 187B and 187A.

The sepals are 5 per flower, about 2.5 to about 4.4 cm. in length and about 0.8 to about 1.3 cm. in width at the widest point. The outer surface color of the sepal is between 137C and 147C sometimes lightly suffused, especially on the side exposed to the sun, with between 187B and 187A. The outer surface of the sepal is somewhat rough and bears between 0 to 7 foliaceous appendages with few stipitate glands, and some hairs. The inner surface color of the sepal is near 146D broadly bordered by near 137C. After the sepals open, the inner surface color is often heavily suffused, especially on the area exposed to the sun, with between 187B and 187A. The inner surface of the sepal is covered with fine wooly tomentum; sepal margins are entire and lined with few stipitate glands and numerous hairs. The sepals are moderately permanent, and usually spear-shaped in shape with acute apices.

The receptacle of the flower is of somewhat short length (about 0.3 to about 0.6 cm.) and average in caliper (about 0.6 to about 1.0 cm. in diameter). The receptacle is cupped shape in form. Its surface is smooth with very few hairs and stipitate glands and with moderately thick fleshy walls. The receptacle color is between 144B and 148B sometimes moderately suffused, especially on the area exposed to the sun, with between 187B and 187A.

As the petals open (after the calyx breaks), the bud is about 1.4 to about 2.1 cm. in diameter at the widest point, about 2.1 to about 3.1 cm. in length, and somewhat pointed to moderately ovoid in form. The color of the under surfaces of the newly opened petals is between 187B and 53A to as dark as between 187A and 59A. At the point where the petal attaches, there is a small zone of between 145A and 144D. The color of the upper surfaces of the newly opened petals is between 187B and 53A to as dark as between 187A and 59A. At the point where the petal attaches, there is a somewhat large zone of between 4B and 5C.

Bloom

When fully open, the bloom ranges from about 8.6 to about 14.3 cm. in diameter. Petalage is very double with about 24 to 58 petals and about 2 to 16 petaloids irregularly arranged. When partially open, the bloom form is ovoid to somewhat cupped, and the petals are moderately tightly spiraled to somewhat cupped to sometimes slightly undulated with petal edges somewhat reflexed outward on the outermost petals and somewhat reflexed inward on the intermediate and inner petals. When fully open, the bloom form is more cupped, and the petals are loosely cupped to sometimes slightly undulated with petal edges somewhat reflexed outward on the outermost petals and somewhat reflexed inward on the intermediate and inner petals.

Petals

The substance of the petals is moderately heavy and of somewhat thin thickness, with upper surfaces moderately satiny and under surfaces moderately shiny. The petals are about 3.6 to about 6.0 cm. in length and about 2.6 to about 6.5 cm. in width at the widest point. Petal margins are entire.

The outer petals are nearly rounded to somewhat obovate in shape with rounded apices and sometimes slightly notched with one notch.

The inner petals are broadly obovate in shape with rounded apices and sometimes slightly notched with one notch.

Petaloids are about 0.8 to about 4.7 cm. in length and about 0.4 to about 3.7 cm. in width at the widest point. Petaloids are irregularly shaped moderately oblanceolate to somewhat subulate with rounded to sometimes lacerated apices.

Newly Opened Flower

The under-surface color of the outer petals is between 60B and 53C. At the point where the petal attaches, there is a small zone of between 2B and 1B. The upper surface color of the outer petals is between 53B and 53C. At the point where the petal attaches, there is a somewhat large zone of between 12A and 13B.

The under-surface color of the intermediate and inner petals is between 60A and 53C. The upper surface color of the intermediate and inner petals is between 53B and 53C.

The under and upper surface colors of the petaloids are similar in coloration to the upper and under surfaces of the intermediate and inner petals.

The general tonality of the newly opened flower is between 53B and 53C.

Three-Day-Old Flower

The under-surface color of the outer, intermediate and inner petals is between 60D and 53C. At the point where the petal attaches, there is a small zone of between 2D and 1D. The upper surface color of the outer, intermediate and inner petals is between 57A and 53C. At the point where the petal attaches, there is a somewhat large zone of between 10B and 11B.

The under and upper surface colors of the petaloids are similar in coloration to the upper and under surfaces of the intermediate and inner petals.

The general tonality of the three-day-old flower is between 57A and 53C.

On the spent bloom, the petals usually drop off cleanly.

In November in Wasco, California, blooms on the bush growing outdoors generally last about four to five days. Cut roses from plants grown outdoors and kept at normal indoor living temperatures generally last about four to five days.

Male Reproductive Organs

Stamens are many in number (average about 140) and are arranged regularly about the pistils; a few are mixed with petaloids. The filaments are of medium to moderately long length (about 0.4 to about 1.1 cm.) most with anthers. Filaments are between 12B and 11A in color. The anthers are medium to somewhat large for the class and all open approximately at the same time. Anther color when immature is near 20A on the external part and near 18D on the internal part. Anther color at maturity is near 164C on the external part and near 200A on the internal part. Pollen is sparse and between 19C and 18C in color.

Female Reproductive Organs

Pistils vary in number (average about 95). The styles are moderately even, somewhat short to average in length (about 0.4 to about 0.9 cm.), average in caliper, and loosely bunched. Stigma color is between 16C and 18A. Style color is between 1C and 154C usually heavily suffused with between 53B and 53C. Ovaries are usually all enclosed in the calyx. The ovaries are of small to medium size and between 158A and 158B in color.

Hips have not been observed on this variety when grown in Wasco, California.

Foliage

The compound leaves are usually comprised of three to five leaflets and are borne abundantly. The five-leaflet leaves are about 10.2 to about 15.9 cm. in length and about 7.0 to about 13.5 cm. in width at the widest point, moderately leathery to somewhat crisp in texture on both sides, and very glossy in finish on the upper side and somewhat glossy in finish on the underside. The leaves have a pinnate venation pattern. The terminal leaflets are about 4.5 to about 7.6 cm. in length and about 3.0 to about 5.0 cm. in width at the widest point, shaped ovate with acute to somewhat acuminate apices and rounded to somewhat cordate bases. Their margins are usually simply serrate.

The upper surface color of the mature leaf is between 139A and 147A. The under-surface color of the mature leaf is between 147B and 146A. The under and upper colors of the leaf veins on the mature leaf are similar in coloration to the upper and under surfaces colors of the mature leaf. The upper surface color of the young leaf is between 137C and 147A, often heavily suffused with between 187A and 187B. The under-surface color of the young leaf is between 147B and 146A, often heavily suffused with between 187B and 187C. The under and upper colors of the leaf veins on the young leaf are similar in coloration to the upper and under surfaces colors of the young leaf.

The rachis is about 3.0 to about 5.3 cm. in length, about 0.1 to about 0.2 cm in width at the widest point, and mostly smooth to sometimes moderately rough. The upper side is moderately shallowly grooved with few hairs and few stipitate glands on the edges of the grooves. The under side of the rachis is mostly smooth to sometimes moderately rough with sometimes few stipitate glands and small prickles. The rachis color is near 149C on the under side and near 137C on the upper side, often heavily suffused on the young leaves with between 187B and 187A.

The stipules are about 1.1 to about 1.7 cm. in length and medium in width to somewhat wide (about 0.6 to about 1.2 cm.) with medium length to somewhat long straight points that usually turn out at an angle of more than 45 degrees and often recurve toward the stem. The under and upper surface color of the stipule is between 137A and 139A often moderately suffused on the young leaves with between 187B and 187C. The upper and under surfaces of the stipules are smooth in texture.

The petiole is somewhat light to average in caliper and mostly smooth to sometimes moderately rough. The upper side is moderately shallowly grooved with few hairs and few stipitate glands on the edges of the grooves. The under side of the petiole is mostly smooth to sometimes moderately rough with sometimes few stipitate glands and small prickles. The petiole is about 0.6 to about 2.0 cm. in length and about 0.1 to about 0.2 cm in width at the widest point. The petiole color is near 149C on the underside and near 137C on the upper side, often heavily suffused on the young leaves with between 187B and 187A.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Wasco, California. The plant's winter hardiness and drought/heat tolerance are yet to be determined.

Growth

The plant has an upright slightly spreading medium height to somewhat tall growing habit (about 107 to about 163 cm. in height and about 102 to about 127 cm. spread at the widest point), with full branching. It displays vigorous growth and the canes are of medium to somewhat heavy caliper for the class (about 1.3 to about 2.2 cm. in diameter at the widest point).

The color of the major stems is between 137A and 137B. The major stems are rough in texture and they bear few large prickles that are about 0.5 to about 0.9 cm. in length. The large prickles are angled slightly downward with a somewhat short to medium length moderately narrow oval base; prickle color is between 165B and 164A sometimes lightly suffused with near 201D. The major stem bears many small prickles of similar shape and coloration.

The color of the branches is between 146B and 137C. The branches are rough in texture and they bear few large prickles which are of similar size and shape to the large prickles on the major stems; prickle color is between 152C and 152B sometimes lightly suffused with near 187C. The branches bear many small prickles of similar shape and coloration.

The color of the new shoots is between 137C and 146A often heavily suffused with between 187A and 187B. The new shoots are rough in texture and they bear few large prickles which are of similar size and shape to the large prickles on the major stems; prickle color is between 145A and 146C often heavily suffused with between 187B and 187C. The shoots bear many small prickles of similar shape and coloration.

I claim:

1. A new and distinct Hybrid Tea rose plant of the variety designated 'WEKamyldroder' substantially as described and illustrated herein.

* * * * *

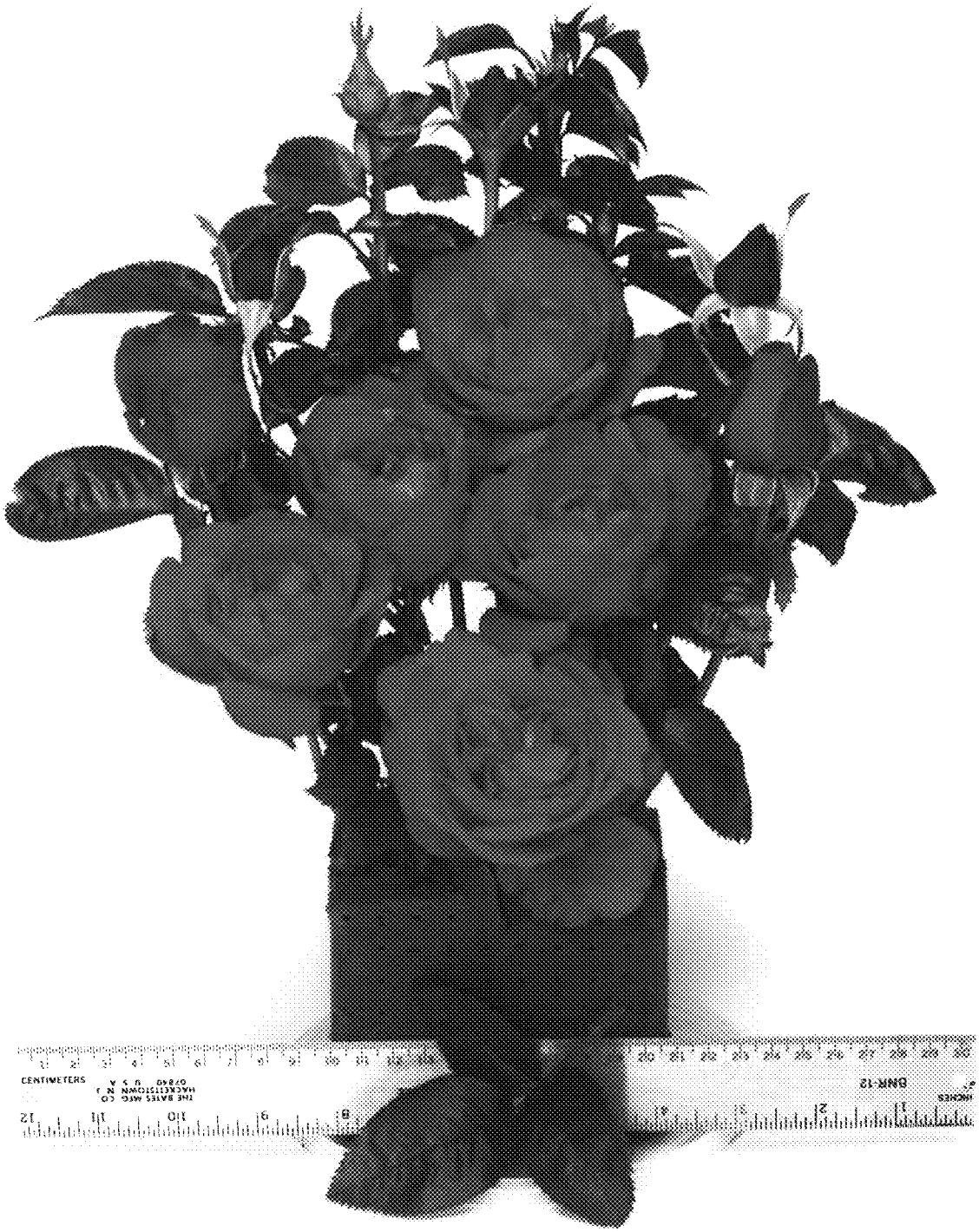
CENTIMETERS
INCHES